United States Patent
Merz

(10) Patent No.: US 9,606,079 B2
(45) Date of Patent: Mar. 28, 2017

(54) INTEGRATED CIRCUIT WITH SENSORS AND MANUFACTURING METHOD

(71) Applicant: NXP B.V., Eindhoven (NL)

(72) Inventor: Matthias Merz, Leuven (BE)

(73) Assignee: NXP B.V., Eindhoven (NL)

( * ) Notice: Subject to any disclaimer, the term of this patent is extended or adjusted under 35 U.S.C. 154(b) by 79 days.

(21) Appl. No.: 13/924,218

(22) Filed: Jun. 21, 2013

(65) Prior Publication Data

US 2013/0341734 A1    Dec. 26, 2013

(30) Foreign Application Priority Data

Jun. 21, 2012  (EP) ................................. 12172984

(51) Int. Cl.
| | |
|---|---|
| *G01N 27/26* | (2006.01) |
| *G01N 27/414* | (2006.01) |
| *H01L 21/82* | (2006.01) |
| *B01L 3/00* | (2006.01) |

(52) U.S. Cl.
CPC ............ *G01N 27/26* (2013.01); *B01L 3/5085* (2013.01); *G01N 27/4145* (2013.01); *G01N 27/4148* (2013.01); *H01L 21/82* (2013.01); *B01L 2200/12* (2013.01); *B01L 2300/0645* (2013.01); *B01L 2300/0819* (2013.01); *B01L 2300/0893* (2013.01)

(58) Field of Classification Search
CPC ...................................................... H01L 21/82
See application file for complete search history.

(56) References Cited

U.S. PATENT DOCUMENTS

| | | | |
|---|---|---|---|
| 7,554,134 B2 | 6/2009 | Cummins | |
| 2005/0156207 A1* | 7/2005 | Yazawa et al. | ............... 257/288 |
| 2010/0137143 A1* | 6/2010 | Rothberg et al. | ................ 506/2 |
| 2010/0248209 A1 | 9/2010 | Datta et al. | |
| 2012/0085660 A1 | 4/2012 | Rothberg et al. | |
| 2013/0334619 A1 | 12/2013 | Merz et al. | |

FOREIGN PATENT DOCUMENTS

| | | |
|---|---|---|
| CN | 1065727 A | 10/1992 |
| CN | 1961209 A | 5/2007 |
| CN | 10148978 A | 7/2009 |
| EP | 2 416 147 A1 | 2/2012 |

OTHER PUBLICATIONS

Extended European Search Report for Patent Appl. No. 12172984.2 (Dec. 7, 2012).
Office Action from counterpart application CN201310246969.2 (Jan. 6, 2015).

* cited by examiner

*Primary Examiner* — Kenneth Parker
*Assistant Examiner* — Christopher Culbert

(57) ABSTRACT

Disclosed is an integrated circuit comprising a substrate (10) carrying plurality of circuit elements (20); a plurality of sensing electrodes (34) over said substrate, each sensing electrode being electrically connected to at least one of said circuit elements; and a plurality of wells (50) for receiving a sample, each sensing electrode defining the bottom of one of said wells, wherein each sensing electrode comprises at least one portion (34') extending upwardly into said well. A method of manufacturing such an IC is also disclosed.

16 Claims, 4 Drawing Sheets

INTEGRATED CIRCUIT WITH SENSORS AND MANUFACTURING METHOD

CROSS-REFERENCE TO RELATED APPLICATIONS

Figure 1:
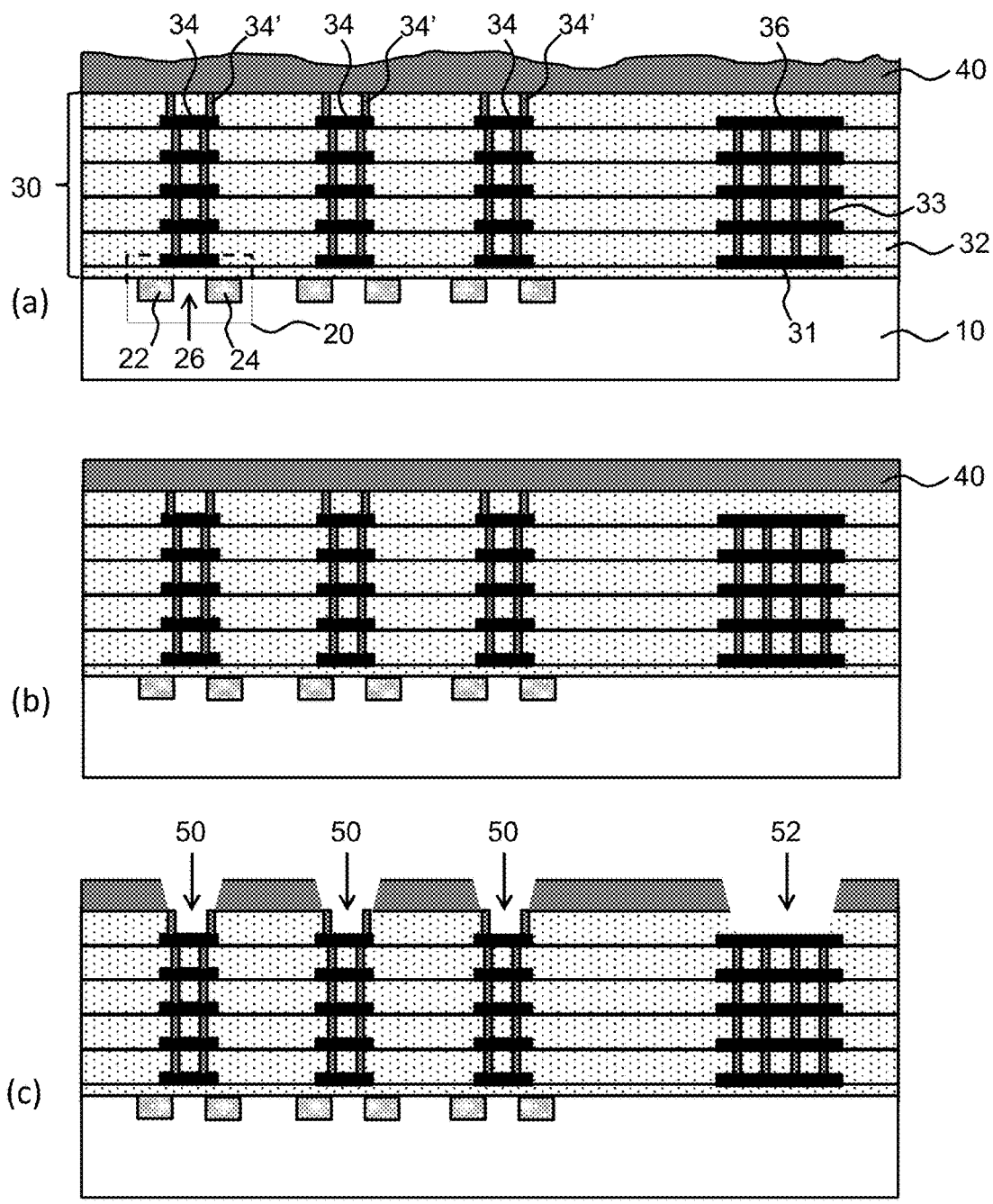
Figure 1:
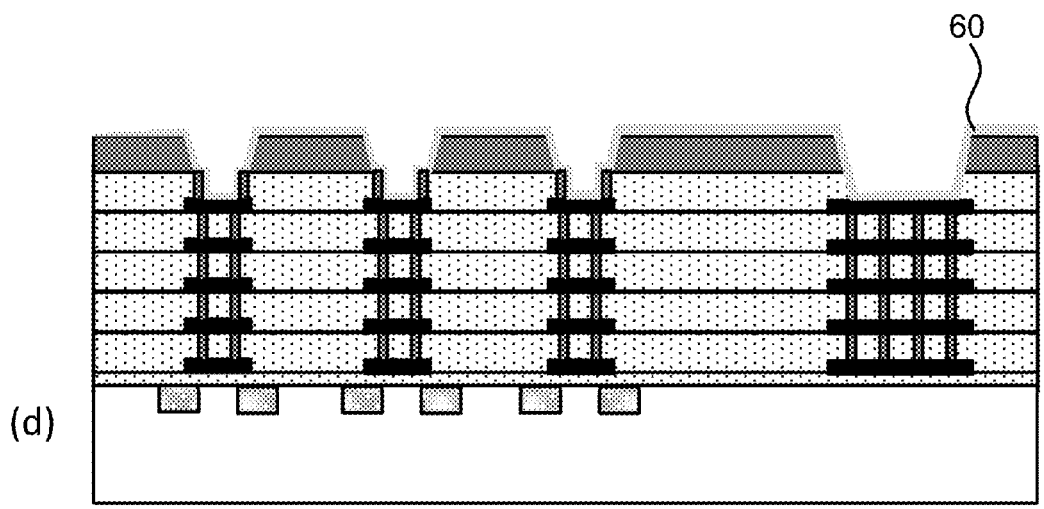

This application claims the priority under 35 U.S.C. §119 of European patent application no. 12172984.2, filed on Jun. 21, 2012, the contents of which are incorporated by reference herein.

FIELD OF THE INVENTION

The present invention relates to an integrated circuit (IC) comprising a plurality of ion-sensitive electrodes in the metallization stack of the IC.

The present invention further relates to a method of manufacturing such an IC.

BACKGROUND OF THE INVENTION

The on-going diversification of IC functionality has led to the miniaturization of many techniques, i.e. has made many techniques available on an IC. Examples of such miniaturization include (medical) laboratory techniques such as analyte analysis of bodily fluid samples and DNA sequencing techniques.

An example of a lab-on-chip device for the monitoring of DNA sequencing is disclosed in US 2010/0137143 A1. This document discloses a CMOS IC in which a plurality of pH-sensitive electrodes, i.e. pH-sensitive gate electrodes of a plurality of ChemFETs or ISFETs is located in the upper metal layer of the metallization stack of the IC. A passivation layer is formed over the metallization stack, with a plurality of silicon dioxide reaction chambers formed on the passivation stack over respective pH-sensitive gate electrodes. Each reaction chamber contains a bead to which a nucleic acid such as a sequencing primer or a self-priming nucleic acid template is covalently bound, with the FETs detecting changes in pH resulting from the release of $H^+$-ions by the hydrolysis of the inorganic pyrophosphate released when a DNA sequence is extended.

The indirect detection of such DNA sequencing by means of monitoring pH changes is particularly promising because it allows for a more facile detection of single extensions to the DNA strand compared to direct detection methods in which capacitive changes due to such extensions are being monitored.

However, the IC disclosed in US 2010/0137143 A1 has a number of notable drawbacks. Firstly, it requires a relatively large number of additional process steps to manufacture, which adds to the cost of the IC. It is for instance well known per se that for extended gate FETs and ISFETs the signal to noise ratio decreases for decreasing surface area of the sensor electrode The fact that the passivation layer is used as the pH sensitive material on the extended gate electrodes of the field effect transistors (FETs) in the metallization stack is a further concern as it limits the materials that can be used for the passivation layer to pH-sensitive materials and moreover limits the sensitivity of the FETs due to the fact that the passivation layer is required to have a minimum thickness in order to effectively protect the underlying structures of the IC from external influences.

SUMMARY OF THE INVENTION

The present invention seeks to provide an IC comprising a plurality of electrodes in the metallization stack of the IC that have improved sensitivity.

The present invention further seeks to provide a method of manufacturing such an IC at a reduced cost.

In accordance with an aspect of the present invention, there is provided an integrated circuit comprising a substrate carrying plurality of circuit elements; a plurality of sensing electrodes over said substrate, each sensing electrode being electrically connected to at least one of said circuit elements; and a plurality of wells for receiving a sample, each sensing electrode defining the bottom of one of said wells, wherein each sensing electrode has at least one portion extending upwardly from the surface of said electrode into said well. The present invention is based on the realization that by extending the area of the electrodes upwards into the wells, e.g. as part of, on, or substantially adjacent to the sidewalls of the sample wells, the area of the electrode can be significantly increased. This therefore allows for a further miniaturization of the sample wells as the larger electrodes improve the signal to noise ratio of the sensor signal generated by the electrodes, thus facilitating the reduction of the dimensions, e.g. the cross-section or diameter, of the wells to sub-micron dimensions, which allows for a higher density of sensing electrodes on a single IC.

In an embodiment, each sensing electrode comprises an ion-sensitive layer such as a pH-sensitive layer. A particularly suitable pH-sensitive material comprises $Ta_2O_5$ as this also is particularly moisture impenetrable, and moreover has very good linearity of electrical response in a large pH range.

Preferably, the IC further comprises a metallization stack over said substrate for providing interconnections to at least some of said circuit elements, the metallization stack comprising a plurality of patterned metal layers spatially separated from each other by respective electrically insulating layers, at least some of said electrically insulating layers comprising conductive portions for electrically interconnecting portions of adjacent metal layers, wherein at least one of the patterned metallization layers comprises the plurality of sensing electrodes, wherein some of said conductive portions define said upwardly extending electrode portions; and wherein the plurality of wells extend into said metallization stack, each well terminating at one of said sensing electrodes.

The provision of sample volumes into the metallization stack has the advantage that the IC may be manufactured in fewer processing steps, whilst at the same time providing sample volumes that can be kept small enough to allow large numbers, e.g. $10^6$ or more, sample volumes to be integrated on the IC. Moreover, the formation of the sidewall extensions of the sample electrodes by means of the interlayer connection portions, e.g. vias, means that the IC with the extended area sensing electrodes may be formed without requiring additional steps in a conventional manufacturing process, e.g. a CMOS process, as the sidewall extensions can be added by altering an existing via formation step rather than requiring an additional process step.

The IC may further comprise a patterned passivation layer comprising a plurality of said apertures, each aperture forming part of a respective sample volume to provide additional protection to the IC.

In a preferred embodiment, the metallization stack further comprises a first patterned metal layer and a second patterned metal layer over the first patterned metal layer, said first patterned metal layer comprising the plurality of sensing electrodes and the second patterned metal layer comprising a plurality of further apertures, each well extending from one of said further apertures to at least one of the sensing electrodes. The second patterned metal layer acts as a mask for the formation of the wells, which has the advantage that high resolution etching of the passivation layer (if present) and the upper dielectric layer(s) of the metallization stack can be achieved without requiring a planarization step prior to the patterning of the passivation layer, which significantly reduces the number of additional process steps as it simply requires an adjustment of the existing first metal layer patterning step rather than an additional patterning step, whilst omitting a planarization step by modifying the existing etch process for opening the bond pads such that the wells through the further apertures is facilitated at the same time. The presence of the second patterned metal layer has the further advantage that the second patterned metal layer acts as a (diffusion) barrier layer for e.g. water and ions, as metals typically exhibit favourable diffusion barrier properties.

Advantageously, the second patterned metal layer is conductively coupled to a bias voltage source. It has been found that the application of such a bias voltage improves the wettability of the well, which is especially advantageous when filling the sample volume with reagents of interest.

In an embodiment, the metallization stack further comprises a passivation layer formed in between adjacent metal layers. This facilitates the removal of a passivation layer on top of the metallization stack, thus improving the protection of the IC against e.g. moisture ingress as the embedded passivation layer requires minimal patterning. Such an embedded passivation layer may be combined with a further passivation layer on top of the metallization stack to e.g. improve the mechanical protection of the IC.

Preferably, each well has tapered sidewalls as it has been found that this makes it easier to fill each sample volume with the reagents of interest, and to retain beads to which a nucleic acid is attached within the well.

Preferably, each well has a rectangular cross-section as this ensures that reagents can still access the well when (substantially) spherical beads are included therein.

Alternatively, the upwardly extending electrode portions may be laterally separated from the sidewalls of the wells to provide access to the wells after loading each well with such a bead. The upwardly extending electrode portions are preferably separated from each other to facilitate the loading of such a bead into a well.

Each well may be filled with one bead, each of said beads comprising a nucleic acid chemically bound to said bead. This allows for the monitoring of DNA replication essentially as disclosed in US 2010/0137143 A1.

In accordance with another aspect, there is provided a method of manufacturing an integrated circuit, the method comprising providing a substrate carrying a plurality of circuit elements; providing a plurality of sensing electrodes over said substrate, each sensing electrode being electrically connected to at least one of said circuit elements; forming a further layer over the plurality of sensing electrodes; opening said further layer to define a plurality of wells for receiving a sample, each of said wells terminating at one of the sensing electrodes; and extending said sensing electrodes by forming conductive portions that extend upwardly into said wells.

As previously explained, by forming the sensing electrodes substantially along, on or in the sidewalls of the wells the area of the sensing electrodes within each well is increased, thus allowing for smaller wells to be formed whilst maintaining an acceptable signal-to-noise ratio in the signals generated by the sensing electrodes.

In embodiment, the method further comprises lining each well with an ion-sensitive dielectric layer following the formation of said conductive portions to provide ion sensitivity to the sensing electrodes.

In a preferred embodiment, the method further comprising providing a metallization stack over said substrate for providing interconnections to at least some of said circuit elements, the metallization stack comprising a plurality of patterned metal layers spatially separated from each other by respective electrically insulating layers, at least some of said electrically insulating layers comprising conductive portions for electrically interconnecting portions of adjacent metal layers, wherein at least one of the patterned metallization layers comprises the plurality of sensing electrodes, some of said conductive portions forming the upwardly extending sensing electrode portions; wherein the further layer comprises at least the upper electrically insulating layer of the metallization stack. As explained above, this has the advantage that the IC may be manufactured in fewer processing steps, whilst at the same time providing sample volumes that can be kept small enough to allow large numbers, e.g. $10^6$ or more, sample volumes to be integrated on the IC.

The method may further comprise providing a planarization layer over the metallization stack and planarizing the passivation layer prior to said patterning step, wherein said opening step comprises forming a plurality of apertures extending through said passivation layer and terminating on one of said electrodes, each of said apertures forming at least a part of one of said wells. In this embodiment, the planarizing step is necessary to facilitate a high-resolution patterning step of the passivation layer.

However, in a preferred alternative embodiment, the metallization stack further comprises a first patterned metal layer and a second patterned metal layer over the first patterned metal layer, said first patterned metal layer comprising the plurality of electrodes and the second patterned metal layer comprising a plurality of further apertures, wherein the step of forming the plurality of apertures further comprises extending each well through one of the further apertures such that said sample volume terminates at one of the sensing electrodes, as in this case a high-resolution lithography step can be achieved more easily as well as without having to first planarize the passivation layer.

BRIEF DESCRIPTION OF THE EMBODIMENTS

Figure 2:
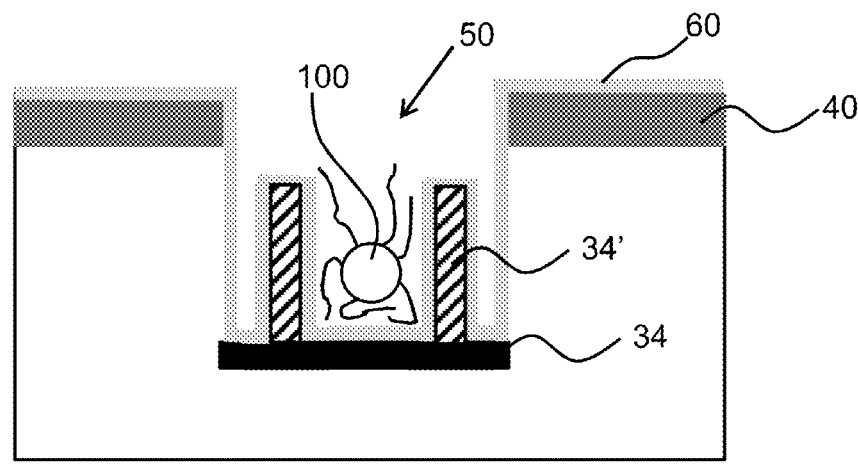
Figure 3:
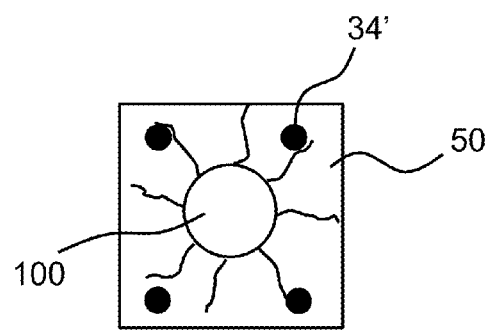
Figure 4:
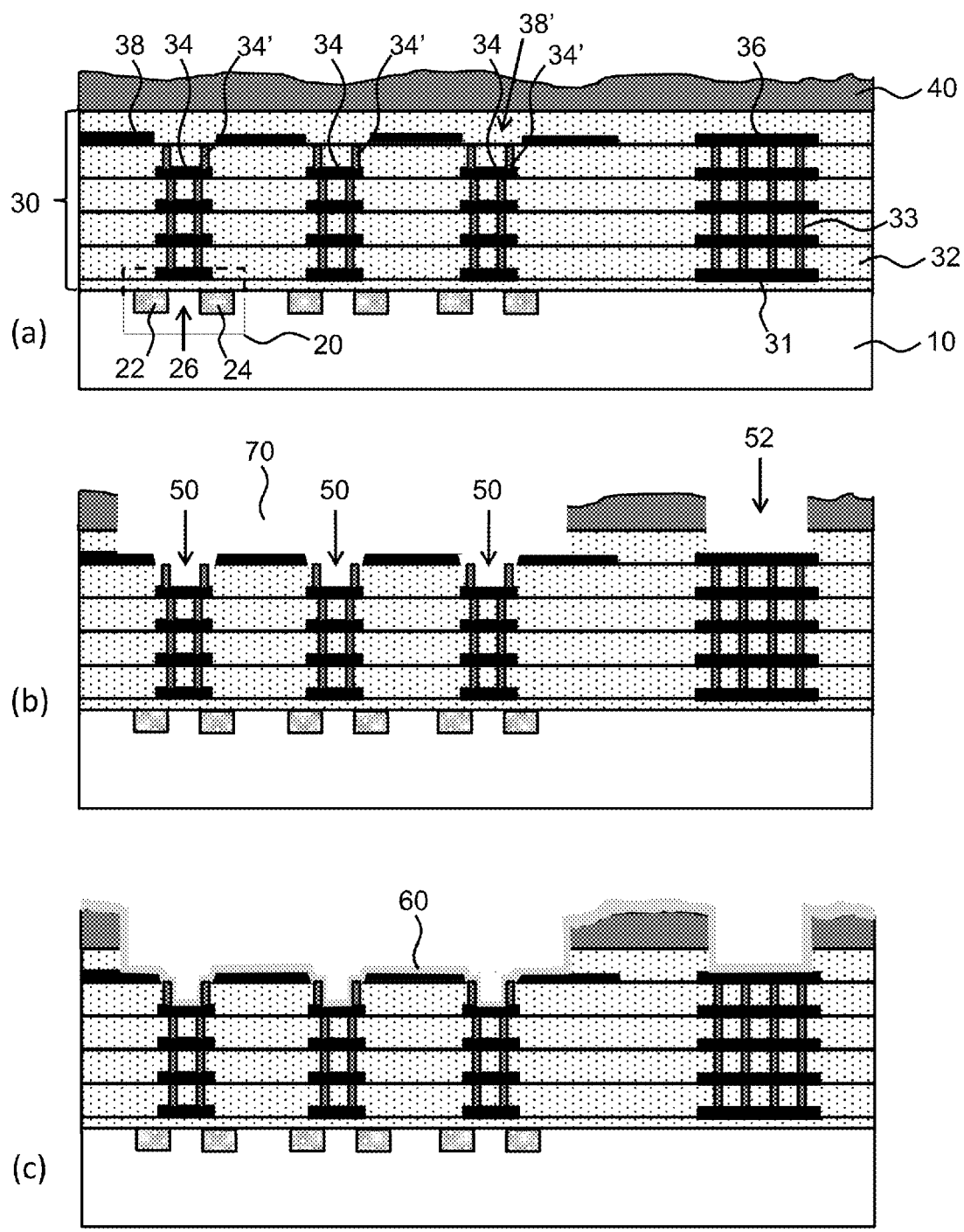
Figure 5:
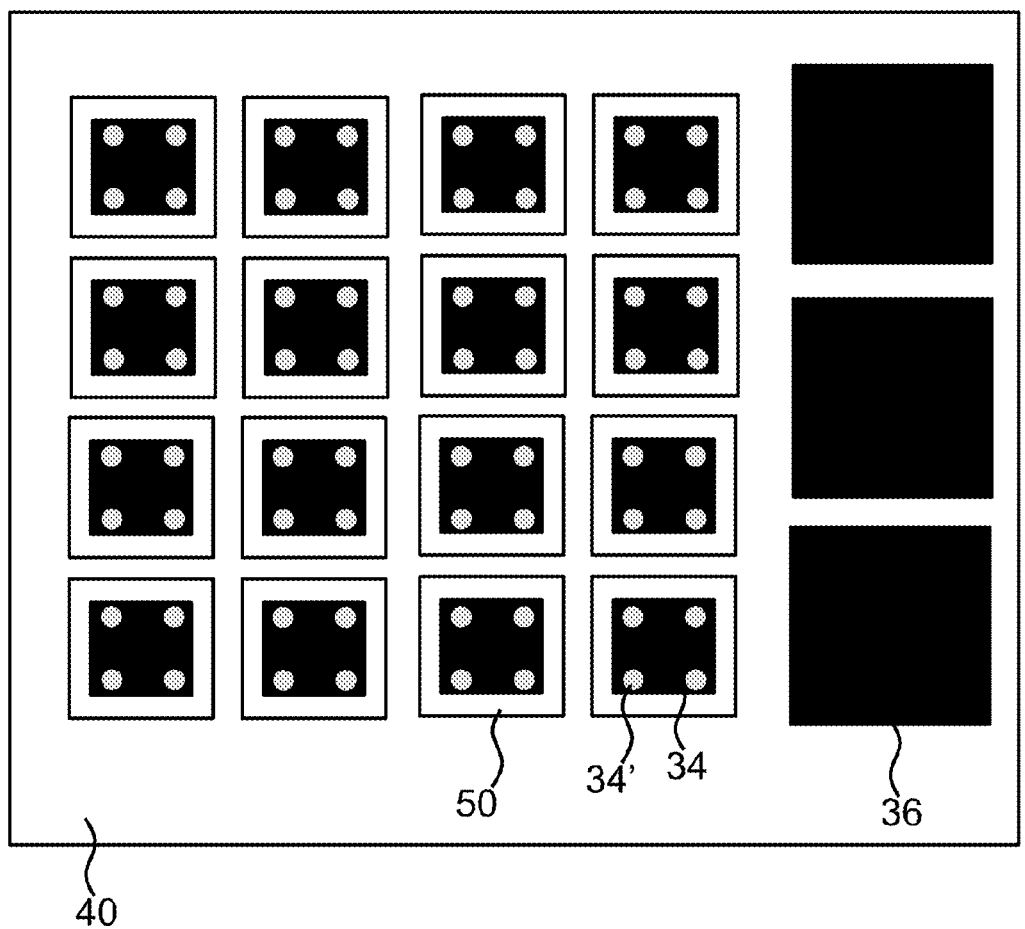

Embodiments of the invention are described in more detail and by way of non-limiting examples with reference to the accompanying drawings, wherein:

FIG. 1 schematically depicts an embodiment of a method of the present invention;

FIGS. 2 and 3 schematically depict a cross section and a top view respectively of a sensing well of an IC of the present invention loaded with a bead;

FIG. 4 schematically depicts an alternative embodiment of a method of the present invention; and FIG. 5 shows a top view of an IC according to an embodiment of the present invention.

DETAILED DESCRIPTION OF THE DRAWINGS

It should be understood that the Figures are merely schematic and are not drawn to scale. It should also be understood that the same reference numerals are used throughout the Figures to indicate the same or similar parts.

FIG. 1 schematically depicts an embodiment of a method according to the present invention for manufacturing an IC comprising a plurality of ion-sensitive electrodes such as pH-sensitive electrodes in the back end of line (BEOL), more specifically in the metallization stack of the IC. Preferably, the IC is manufactured in a CMOS process although any suitable semiconductor technology may be used to manufacture an IC according to an embodiment of the present invention.

The first step (a) shown in FIG. 1 is entirely conventional, and includes the provision of a suitable substrate 10 comprising, e.g. carrying, a plurality of semiconductor circuit elements 20 such as field effect transistors or the like. The substrate 10 may be any suitable substrate, e.g. a substrate comprising Si, SiGe, GaAs or GaN, a silicon on insulator substrate and so on. In FIG. 1 a lateral FET 20 is shown having a source region 22, a drain region 24 and a channel region 26 extending from the source region 22 to the drain region 24. It should be understood that a lateral FET is shown by way of non-limiting example only and that other transistor designs, e.g. vertical FETs, bipolar transistors, non-transistor semiconductor devices and so on, are equally feasible. Such semiconductor circuit elements are well-known per se and may be manufactured using any suitable process steps. As a plethora of suitable process steps are known to the skilled person, this will not be further discussed for the sake of brevity.

A metallization stack 30 is formed on the substrate 10 to provide interconnections to and/or between the semiconductor circuit elements 20. The metallization stack typically comprises a plurality of patterned metal layers 31 that are electrically insulated from each other by dielectric layers 32, with portions of different metal layers 31 electrically interconnected through vias 33. The provision of such a metallization stack 30 is again well-known per se and may be achieved in any suitable manner.

It is noted that in case of a CMOS process, any suitable material may be used to form the metallization stack, such as Ti, TiN, Al, Cu and combinations thereof to define the metal layers 31 and silicon oxide, silicon nitride, low-k dielectrics and other dielectric materials as well as combinations thereof to form the dielectric layers 32. Although in FIG. 1(a) these layers are depicted as single layers, it should be understood that these layers themselves may comprise a stack of layers, as is common design practice in contemporary semiconductor technologies such as sub-micron CMOS technologies.

The metallization stack 30 comprises a plurality of sensing electrodes 34 that are electrically connected to respective circuit elements 20, and may further comprise additional interconnection structures such as one or more bond pads 36. In a preferred embodiment, each electrode 34 is an extended gate of an extended gate field effect transistor (EGFET) 20. In an alternative embodiment, each electrode 34 forms a capacitive plate of a capacitor having the medium over the electrode 34 as the opposite capacitive plate and a dielectric layer in between both plates, in which case the circuit element 20 may be adapted to detect capacitance changes using alternating currents. In yet another embodiment, each electrode 34 is connected, e.g. by a connection to the metallization structure in between the electrode 34 and the circuit element 20 to a further switch, e.g. a FET, for providing a defined potential to the sensing electrode 34, such that the electrode can be pre-charged to a set operating point. As such sensing principles are known per se, they will not be discussed in further detail for the sake of brevity.

In accordance with an embodiment of the present invention, some of the vias 33 are formed on the sensing electrodes 34 to form upwardly extending portions 34' of these electrodes, as will be explained in more detail below. It is important to realize that such upwardly extending via portions 34' may be included in an already existing via formation step by redesigning this step, such that the upwardly extending portions 34' can be added to the IC design without the need to include additional processing steps to the formation of the metallization stack 30. Each sensing electrode 34 may comprise any suitable number of upwardly extending portions 34'. In case of such portions 34' being formed by vias 33, the vias may be shaped as pillars upwardly extending from the surface of the sensing electrode 34. Any suitable number of such pillars may be included within a single well over the sensing electrode 34; generally speaking it may be advantageous to maximize the number of such upwardly extending portions within a single well to maximize the increase in the area of the sensing electrode 34.

In an embodiment, a passivation layer 40 is typically formed over the metallization stack 30 using any suitable deposition technique. Any suitable passivation material or combination of passivation materials may be used for the passivation layer 40. Although in the present application the passivation layer 40 is shown as a single layer, it should be understood that it is equally feasible that the passivation layer 40 comprises a plurality of layers, e.g. a combination of two or more layers selected from a group of materials at least including silicon oxide ($SiO_2$), silicon nitride, silicon-rich nitride and so on.

In a next step (b), the passivation layer (or layer stack) 40 is planarized using any suitable passivation method. For instance, the passivation layer 40 is planarized using chemical mechanical polishing (CMP). The optional planarization of the passivation layer 40 ensures that the opening of the passivation layer using lithography can be achieved with the desired high resolution. In particular, a planar passivation layer facilitates the formation of a highly conformal (patterned) photoresist, which thus facilitates the formation of structures having a feature size of no more than a few microns.

Next, the passivation layer is patterned, i.e. opened, using a suitable etch recipe, e.g. a suitable dry etch recipe, thereby defining a well or sample volume 50 over each electrode 34 defined by the apertures etched in the passivation layer and the removal of the dielectric material 32 of the metallization stack 30 over the electrodes. The wells 50 are formed such that one or more upwardly extending portions 34' of each sensing electrode 34 are formed inside the wells 50. At the same time, the bond pads 36 may be exposed by the formation of an opening 52 over the bond pads 36. This is shown in step (c). As the patterning of passivation layers is well-known per se, this will not be explained in further detail for the sake of brevity. The etch recipe may be adjusted at the latter stages of the etch process to facilitate the selective removal of the dielectric material of the passivation stack 30 where necessary, e.g. using a gas mixture including $CF_4/O_2$ or any other suitable etch recipe. Such etch recipes typically have excellent selectivity between the dielectric layers of the metallization stack 30 on the one hand and the metal layers of the metallization stack 30 on the other hand.

In an embodiment, the upwardly extending portions 34' are laterally separated from the side walls of the wells 50. In an alternative embodiment, the upwardly extending portions 34' form at least a part of the side walls of the wells 50.

In an embodiment, the apertures have a rectangular cross-section, e.g. a square cross-section for reasons that will be explained in more detail below.

In another embodiment, the wells or sample volumes 50 have tapered side walls. As is known per se, the side wall shape may be controlled by tuning the dry etch conditions; e.g. optimizing the bias voltage and gas composition, e.g. to control the formation of protective polymers at sidewalls. The sidewalls that taper inwardly from the top of the passivation layer 40 towards the electrodes 24 for reasons that will be explained in more detail below. The wells or sample volumes 50 may include both the rectangular cross-section and the tapered side walls.

In an alternative embodiment, the formation of the passivation layer 40 on top of the metallization stack 30 is omitted from the method of the present invention. In this embodiment, the sample volumes 50 may be formed in the upper dielectric layer(s) 32 of the metallization stack 30, whilst terminating each sample volume on an electrode 34. To provide protection of the circuit elements 20 against the environment, e.g. moisture ingress, a passivation layer or other suitable moisture barrier may instead be integrated in the metallization stack 30, i.e. by choosing one of the intermediate dielectric layers 31 for this purpose.

This may for be achieved by forming the planarized passivation layer 40 as shown in step (b) of FIG. 1 but forming one or more additional metal layers 32 and dielectric layers 31 on top of the passivation layer 40, thereby extending the metallization stack 30, with the electrodes 34 formed in at least one of these additional metal layers 32. Electrically conductive portions 33, e.g. vias may be formed through the passivation layer 40 in this embodiment to provide the interconnection between the metal layers directly above and below the passivation layer 40.

In step (d), a relatively thin dielectric layer 60 is deposited over the resultant structure to add the ion-sensitivity to the electrodes 34 including the upwardly extending portions 34'. In a preferred embodiment, the dielectric layer 60 has a thickness in the range of 20-200 nm. In a more preferred embodiment, the dielectric layer 60 has a thickness in the range of 40-80 nm. If the dielectric layer 60 has a thickness of more than about 200 nm, the sensitivity of the electrode 34 may be insufficient. If the dielectric layer has a thickness of less than about 20 nm, pin holes may form in the dielectric layer such that the dielectric layer 60 no longer protects the underlying circuit elements 20 and metallization stack 30 from the environment, e.g. moisture ingress.

In yet another embodiment, a passivation layer incorporated into the metallization stack 30 as explained above may be combined with a passivation layer 40 on top of the metallization stack 30 as shown in FIG. 1, in which case the sample volumes 50 may be formed as shown in FIG. 1, e.g. by etching through the passivation layer 40 such that the apertures in the passivation layer 40 form part of the sample volumes 50. In this embodiment, the dielectric layer 60 may also define the additional passivation layer 40.

The dielectric layer 60 may be subsequently patterned in any suitable manner to remove the dielectric layer from areas where this material is not required, e.g. from the surface of the bond pads 36. In an embodiment, the dielectric layer 60 is selected to make the electrodes 34 sensitive to $H^+$ ions, i.e. to make the electrodes 34 pH-sensitive. This makes the IC suitable for monitoring DNA sequencing, as will be explained in more detail below. Suitable dielectric materials for adding pH sensitivity to the electrodes 34 include $Ta_2O_5$, $Al_2O_3$, $SiON$, $Si_3N_4$ and $SiO_2$ amongst others, of which $Ta_2O_5$ is particularly suitable because it is impenetrable to moisture, such that it gives additional protection to the metallization stack 30 and the circuit elements 20. In addition, $Ta_2O_5$ has excellent linearity of electrical response in a large pH range.

The IC may subsequently be finalized, e.g. packaged, in any suitable manner, after which the IC is ready to be used for its intended purpose. In an embodiment, the IC is used to monitor DNA sequencing analogous to the method disclosed in US 2010/0137143 A1. To this end, as shown in FIG. 2, a bead 100 may be provided to which a nucleic acid such as a sequencing primer or a self-priming template nucleic acid is chemically bound, e.g. covalently bound in each of the wells 50. Such beads 100 may be of any suitable material, e.g. an uncoated or epoxide-coated silica bead, a polymer bead and so on. Other suitable bead materials will be apparent to the skilled person. Typically, the beads 100 have a size such that a single bead only will fit into a well or sample volume 50.

In order to functionalize the IC, the dispersion including the beads 100 is deposited over the surface of the IC including the sample volumes 50, after which the IC is subjected to a centrifugation step to force the beads from the dispersion into the sample volumes or wells 50. It has surprisingly been found that the loading of the beads into the sample volumes or wells 50 is particularly successful if the sidewalls of the sample volumes or wells 50 have the aforementioned tapered shape. Ideally, each well 50 comprises a single bead carrying a particular DNA sequence (i.e. multiple copies of the same nucleic acid) although it is sometimes difficult to avoid that some wells or sample volumes remain vacant.

Alternatively, in an embodiment where the upwardly extending electrode portions 34' are laterally separated from the sidewalls of the wells 50, e.g. when the upwardly extending electrode portions 34' are pillar-shaped, the beads may be forced in between the upwardly extending electrode portions 34' by centrifugation, which successfully captures (immobilizes) the beads in the wells 50. Furthermore, the aforementioned lateral separation between the upwardly extending electrode portions 34' and the sidewalls of the wells 50 ensures that reagents can still access the wells 50 even after loading with the beads, such that this embodiment provides a suitable alternative to the rectangular shape of the wells 50 and/or the tapered shape of the side walls of the wells 50.

After removing the excess dispersion, the IC may be used for detecting DNA sequencing events as explained in US 2010/0137143 A1. In short, the four different nucleotides (adenine, guanine, cytosine and thymine) are sequentially fed over the surface of the IC comprising the wells 50 in the presence of suitable enzymes (polymerases). In each cycle, a sequencing reaction may take place if the nucleotide fed over the IC surface complements the available terminal nucleotide of the nucleic acid bound to the single bead in one or more of the wells 50. This sequencing reaction releases inorganic pyrophosphate, which may be hydrolysed to orthophosphate and free hydrogen ions ($H^+$), which causes a change in the pH in the well 50 over an electrode 34 and its upwardly extending portion(s) 34'. In an embodiment, the sensing electrodes 34 are continuously monitored (measured) to ensure that the detection sensitivity of the IC is maximized, in particular by minimizing the risk that generated $H^+$-ions remain undetected as such ions can diffuse quickly out of the sample volumes and therefore can be missed if detection is not continuous.

Hence, at least after each sequencing step, the pH is measured in each well 50 to detect the sample volumes in which a sequencing or hybridization reaction has taken place. This way, the nucleotide sequence of the nucleic acids in each of the wells 50 can be accurately determined. Further details can be found in US 2010/0137143 A1 and the references described therein, such as in paragraph [0034] of this application.

It is advantageous that the wells 50 have a rectangular cross-section, as the beads 100 are typically substantially spherical, such that it is guaranteed that the sample volumes 50 can only be partially filled by such a bead 100, thereby guaranteeing that the reagents, e.g. the nucleotides, can still access the wells 50. In contrast, for a well 50 having an annular cross-section, a substantially spherical bead can essentially block, i.e. entirely occupy, the well 50, thus substantially preventing the reaction between the nucleic acid attached to the bead 100 and the nucleotides flushed over the surface of the IC in the various sequencing steps as explained above. However, as previously explained, this problem may also be avoided by having upwardly extending electrode portions 34', e.g. pillars, which are laterally separated from the sidewalls of the wells 50.

In order to improve the signal-to-noise ratio of the sensing electrodes 34 as much as possible, it is preferred that a plurality of upwardly extending portions 34', e.g. via pillars, is included in each well 50. A non-limiting example is shown in FIG. 3, in which four via pillars 34' are present in a well 50, in between which a bead 100 including nucleic acid strands attached to its surface is present.

At this point it is noted that a particular advantage of the use of discrete upwardly extending portions 34' that are laterally separated from each other, e.g. via pillars, is that the loading of the bead 100 into the well 50 is not significantly impeded by the presence of the upwardly extending portions 34' as e.g. the nucleic acid strands on the surface of the bead 100 can utilize the space between neighbouring portions 34' such that the effective volume of the wells 50 is not significantly reduced by the presence of the discrete and laterally separated upwardly extending portions 34'. It has been found that during loading a bead into a well 50 comprising such laterally separated upwardly extending portions 34', the bead tends to rest on top of the upwardly extending portions 34' when being applied to the surface of the sensing IC, after which a centrifuging step successfully forces the bead in between the upwardly extending portions 34'. In addition, the intimate contact between the bead 100 and the upwardly extending portions 34' ensures that less H$^+$-ions that are released during a sequencing reaction will diffuse out of the wells 50 before they can be detected by the sensing electrodes 34, which provides a further improvement of the signal-to-noise ratio produced by the electrodes.

The pillars 34' can be kept relatively small; for instance, in a CMOS technology with a 140 nm feature size, the diameter of the vias 33 is typically about 250 nm and provides an additional area of about 0.6 $\mu m^2$, such that for a sensing electrode 34 having a surface area of 1 $\mu m^2$, four of such via pillars 33 extending from the electrode surface 34 increase the overall surface area of the sensing electrode 34 to 3.4 $\mu m^2$ without significantly reducing the accessible area of the wells 50.

In FIGS. 2 and 3, the pillars 34 are shown as laterally displaced in respect of the sidewalls of the well 50 by way of non-limiting example only, Such a lateral displacement may be avoided by carefully tuning the etch recipe used to form the wells 50.

However, it is equally feasible to form the upwardly extending portions 34' after the wells 50 have been formed, in which case these portions 34' may be formed on the sidewalls of the wells 50. This has the advantage that the accessible volume of the wells 50 is maximized, but comes at the cost of requiring at least one additional processing step in the manufacturing process of the IC, thus adding to the cost of the IC.

The upwardly extending metal portions 34' may be formed on the sidewalls of the well 50 by a conformal metal deposition after the formation of the wells 50, to cover the bottom and side walls of the wells with the conformal metal layer. An etching step is subsequently applied to remove the conformal metal layer in between wells 50 to prevent short circuits between electrodes 34 in different wells 50. The method subsequently proceeds by the formation of the dielectric layer 60 as previously explained.

FIG. 4 depicts an alternative embodiment of a method of manufacturing such an IC. Step (a) is essentially the same as step (a) of FIG. 1, which has been described in more detail above, such that this description is not repeated for the sake of brevity. The main difference is that in the metallization stack 30, the upper metallization layer 31 comprises a pattern 38 including further apertures 38' over the electrodes 34 and its upwardly extending portions 34' compared in step (a) of FIG. 1 in which the electrodes 34 were located in the upper metal layer of the metallization stack 30. The pattern 38 including apertures 38' defines a hard mask for the formation of the wells or sample volumes 50, as will be explained in more detail below.

In FIG. 4(a), the electrodes 34 are located in the metal layer 31 immediately below the upper metal layer 31 including the pattern 38 by way of non-limiting example only. It should be understood that is equally feasible to include at least some of the electrodes 34 in lower metal layers 31, e.g. in case the depth of the sample volume or well 50 is to be increased. In such an embodiment, it should be understood that patterned metal layers in between the upper metal layer including the pattern 38 and the lower metal layer including the electrodes 34 typically will comprise yet further apertures in between the further apertures 38' and the electrodes 34 such that the sample volumes 50 can extend through said collection of apertures to the electrodes 34.

The apertures 38' are dimensioned such that the hard mask 38 is laterally separated from the upwardly extending portions 34', e.g. via pillars, of the sensing electrodes 34, to avoid a short circuit between neighbouring sensing electrodes 34.

Importantly, the presence of the hard mask formed by the metal pattern 38 in the upper metal layer of the metallization stack 30 obviates the need for a planarization step of the passivation layer 40 to facilitate the high resolution patterning step to form the sample volumes or wells 50. This is feasible to due to the previously mentioned high etch selectivity between the metal and dielectric materials in the metallization stack 30, such that it is furthermore straightforward to terminate the etch step on the sensing electrodes 34. The etch recipe for opening the bond pads 36 can be used to form the sample volumes or wells 50 in this embodiment simply by extending the duration of the etch step, which therefore avoids the need for an additional lithographic step to form the sample volumes 50.

Consequently, in this embodiment, the method may proceed directly to the patterning of the passivation layer 40 and selective removal of the dielectric material 32 to define the wells 50 and the bond pad openings 52 if applicable, as shown in step (b) of FIG. 4. Substantially the same etch recipe as previously described may be used, and only minor alterations of the etch conditions, in particular the etch duration, are required to form the deeper wells 50.

The depth of the wells 50 may be controlled by the thickness of the metal mask 38 and the location of the electrodes 34 as previously explained. It is noted that due to the longer duration of the etch step and the non-planar nature of the passivation layer 40, a relatively large portion 70 of the passivation layer 40 is removed from over the metal mask 38, which portion may define an aperture exposing a plurality of wells 50. However, as each well 50 is now defined downwardly from the metal mask aperture 38', this does not provide any drawback.

After the formation of the wells 50, the thin ion-sensitive dielectric layer, i.e. the electrically insulating film 60 is deposited over the resultant structure as shown in step (c). As already explained in the detailed description of step (d) of FIG. 1, the electrically insulating film 60 may subsequently be selectively removed from those parts of the IC where the film is not required, e.g. from the surface of the bond pads 36. This is not explicitly shown.

In an alternative embodiment (not shown), the passivation layer 40 may be omitted altogether. In this embodiment, the sample volumes 50 are formed directly in the metallization stack 30 using the patterned metal layer 38 as a hard mask. In this embodiment, the subsequently deposited ion-sensitive dielectric layer 60 may also be used as a protection or passivation layer. In yet another alternative embodiment, the passivation layer 40 is integrated in the metallization stack 30, i.e. located in between two intermediate metal layers 32 of the metallization stack 30 as explained in more detail above. A combination of these embodiments is also feasible, i.e. an embodiment in which a first passivation layer is incorporated in the metallization stack and a further passivation layer 40 is present on top of the metallization stack 30, with the sample volumes 50 being formed through the further passivation layer 40 as previously explained.

At this point it is noted that the patterned metal mask 38 in the upper metal layer of the metallization stack 30 may be electrically connected to a bias voltage source, e.g. to a bond pad (not shown) or to one or more circuit elements 20 on the substrate 10, such that during operation of the IC the metal mask 38 may act as a biasing electrode. This is particularly advantageous during the loading of the wells 50 with the nucleic acid containing beads and/or the reagents used in the sequencing process because the applied bias voltage can be used to alter the wetting characteristics of the wells 50, thus improving the transfer properties of such moieties into the wells 50. Moreover, the bias voltage can be used to alter, e.g. increase, the binding characteristics of ions, in particular protons, to the ion-sensitive electrodes 34 including the one or more upwardly extending portions 34', which facilitates improved control over the signal amplitude of each of the circuit elements 20 having an ion-sensitive electrode 34 exposed to the sample.

As in FIG. 1, the wells or sample volumes 50 in FIG. 4 preferably have a rectangular such as a square cross-section and/or tapered side walls, or include upwardly extending electrode portions 34' that are laterally separated from the side walls of the wells 50 for the reasons given above.

FIG. 5 schematically depicts a top view of an embodiment of an IC of the present invention. The IC comprises a plurality of wells or sample volumes 50 accessible through the passivation layer 40 (when present) and having an exposed ion-sensitive electrode 34 at the bottom of the sample volume. Each well further comprises four electrically conductive portions 34' by way of non-limiting example only that extend upwardly from the surface of the sensing electrode 34 to increase the surface area of the sensing electrode. The sample volumes 50 may be organized in a regular pattern, e.g. an array or grid. A plurality of bond pads 36 is also present to provide external contacts to at least some of the circuit elements 20 on the substrate 10 of the IC.

For an IC having dimensions of 1 cm×1 cm and sample volumes 50 having a 1 micron cross section and an 4 micron spacing between adjacent sample volumes, a grid of 2,000× 2,000 sample volumes, i.e. $4 \times 10^6$ sample volumes can be integrated on a single IC. In fact, a higher density can be easily achieved by reducing the sample volume spacing or cross-sections and/or by increasing the dimensions of the IC. Hence, embodiments of the present invention provide a cost-effective method for producing an IC comprising millions of ion-sensitive electrodes, which significantly reduces the cost of producing so-called lab-on-chip ICs, in particular biochips for monitoring DNA sequencing.

In summary, an important advantage of the present invention as described in the above embodiments is that by providing the sensing electrodes 34 with upwardly extending portions 34' that are formed by metal interconnect portions, e.g. via pillars 34', the number of process steps in the manufacturing process of the IC does not need to be (significantly) increased as the vias have to be formed anyway such that the formation of the vias 34' on the sensing electrodes 34 only requires a redesign of some of the existing process steps rather than the introduction of additional process steps to form the upward extensions 34' of the sensing electrodes 34. In particular, the upwardly extending portions 34' may be formed using the same process steps used for defining vias in the lower parts of the metallization stack 30, requiring only a different mask.

However, despite this fact, it should be recognized that the present invention is not necessarily limited to the formation of electrodes with upwardly extending via portions in a metallization stack of an IC. For instance, in a non-limiting alternative embodiment the electrodes 34 may be formed (directly) on the circuit elements 20 and the wells 50 may be formed in any suitable further layer over the electrodes 34, e.g. any suitable electrically insulating layer, e.g. silicon oxide, silicon nitride, a low-k dielectric and so on, by way of a patterning step such as an etching step or a development step in case of the further layer comprising a curable material, e.g. a polymer such as polyimide, after which the electrode extensions 34' may be formed on the sidewalls of such wells 50 by conductively connecting the electrode extensions 34' to the electrode portions 34 at the bottom of the wells, e.g. using any suitable deposition technique such as atomic layer deposition or the like. Although this typically requires an additional manufacturing step to form the upwardly extending portions 34' of the electrodes 34, it nevertheless still allows for an improvement of the signal-to-noise ratio of such electrodes as previously explained. Other variations to the inventive concept of the present invention will be immediately apparent to the skilled person.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or an preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An integrated circuit comprising:
a substrate carrying plurality of circuit elements;
a plurality of sensing electrodes over said substrate, at least one sensing electrode being electrically connected to at least one of said circuit elements;
a plurality of wells for receiving a sample, the at least one sensing electrode defining a bottom of at least one of said wells, wherein the at least one sensing electrode comprises a portion extending upwardly into said well and said portion laterally separated from side walls of the well;
wherein the portion extending upwardly has a first lateral side and a second lateral side; and
wherein the portion extending upwardly is configured to permit the sample to enter between the first lateral side of the portion and a first one of the side walls, and to permit the sample to enter between the second lateral side of the portion and a second one of the side walls.

2. The integrated circuit of claim 1, wherein each sensing electrode comprises an ion-sensitive layer.

3. The integrated circuit of claim 1, further comprising:
a metallization stack over said substrate for providing interconnections to at least some of said circuit elements,
the metallization stack comprising a plurality of patterned metal layers spatially separated from each other by respective electrically insulating layers,
at least some of said electrically insulating layers comprising conductive portions for electrically interconnecting portions of adjacent metal layers,
wherein at least one of the patterned metallization layers comprises the plurality of sensing electrodes,
wherein some of said conductive portions define said upwardly extending sensing electrode portions; and
wherein the plurality of wells extend into said metallization stack, each well terminating at one of said sensing electrodes.

4. The integrated circuit of claim 3, further comprising a patterned passivation layer over said metallization stack, said patterned passivation layer comprises at least one aperture extending through said passivation layer providing access to and/or forming at least a part of one of said wells.

5. The integrated circuit of claim 4, wherein the patterned passivation layer comprises a plurality of said apertures, each aperture forming part of a respective well.

6. The integrated circuit of claim 3, wherein the metallization stack further comprises a first patterned metal layer and a second patterned metal layer over the first patterned metal layer,
said first patterned metal layer comprising the plurality of sensing electrodes and the second patterned metal layer comprising a plurality of further apertures,
each well extending towards one of said sensing electrodes from one of said further apertures.

7. The integrated circuit of claim 6, wherein the second patterned metal layer is conductively coupled to a bias voltage source.

8. The integrated circuit of claim 3, wherein the metallization stack further comprises a passivation layer formed in between adjacent metal layers.

9. The integrated circuit of claim 1, wherein each well has tapered sidewalls and/or a rectangular cross-section.

10. The integrated circuit of claim 1, wherein at least some of said wells contain a bead, each of said beads comprising a nucleic acid chemically bound to said bead.

11. The integrated circuit of claim 1, wherein the portion extending upwardly into said well is shaped as a pillar.

12. A method of manufacturing an integrated circuit, the method comprising:
providing a substrate carrying a plurality of circuit elements;
providing at least one sensing electrode over said substrate, the sensing electrode being electrically connected to at least one of said circuit elements;
forming a further layer over the sensing electrode;
opening said further layer to define a well for receiving a sample, the well terminating at the sensing electrode;
extending said sensing electrode by forming a conductive portion that extends upwardly from the electrode surface into said well, said conductive portion laterally separated from side walls of the well;
wherein the conductive portion has a first lateral side and a second lateral side; and
wherein the conductive portion is configured to permit the sample to enter between the first lateral side of the conductive portion and a first one of the side walls, and to permit the sample to enter between the second lateral side of the conductive portion and a second one of the side walls.

13. The method of claim 12, further comprising lining the well with an ion-sensitive dielectric layer following the formation of said conductive portion.

14. The method of claim 12,
further comprising
providing a metallization stack over said substrate for providing interconnections to at least some of said circuit elements,
the metallization stack comprising
a plurality of patterned metal layers spatially separated from each other by respective electrically insulating layers,
at least some of said electrically insulating layers comprising conductive portions for electrically interconnecting portions of adjacent metal layers,
wherein at least one of the patterned metallization layers comprises the sensing electrode,
some of said conductive portions defining said upwardly extending electrode portion;
wherein the further layer comprises at least the upper electrically insulating layer of said metallization stack.

15. The method of claim 14, further comprising
forming a passivation layer over the metallization stack and
planarizing the passivation layer prior to said patterning step,
wherein said opening step comprises forming a plurality of apertures extending through said passivation layer and terminating on the electrode,
each of said apertures forming at least a part of the well.

16. The method of claim 14,
wherein the metallization stack further comprises a first patterned metal layer and a second patterned metal layer over the first patterned metal layer,
said first patterned metal layer comprising the electrode and the second patterned metal layer comprising a plurality of further apertures, wherein said opening step further comprises forming the well by selectively removing part of the further layer over said electrodes through said at least one of the further apertures.

* * * * *